United States Patent [19]

Hessel et al.

[11] Patent Number: 5,156,604
[45] Date of Patent: Oct. 20, 1992

[54] SMALL PROBING HOOK FOR ARTHROSCOPY

[75] Inventors: Stefan Hessel, München; Patricia Taige, Ottobrunn, both of Fed. Rep. of Germany

[73] Assignee: Messerschmitt-Bolkow-Blohm GmbH, Fed. Rep. of Germany

[21] Appl. No.: 781,320

[22] Filed: Oct. 24, 1991

[30] Foreign Application Priority Data

Oct. 25, 1990 [DE] Fed. Rep. of Germany ....... 4033916

[51] Int. Cl.5 ............................................. A61B 17/36
[52] U.S. Cl. ...................................... 606/15; 606/16; 128/397; 128/398; 128/20
[58] Field of Search ....................... 606/13, 14, 15, 16, 606/17, 19, 2, 149; 128/20, 397, 398

[56] References Cited

U.S. PATENT DOCUMENTS

| 4,049,000 | 9/1977 | Williams | 604/119 |
| 4,240,431 | 12/1980 | Komiya | 606/15 |
| 4,461,283 | 6/1984 | Doi | 606/15 |
| 4,881,524 | 11/1989 | Boebel et al. | 606/15 X |
| 4,985,028 | 1/1991 | Isner et al. | 606/15 |

Primary Examiner—Stephen C. Pellegrino
Assistant Examiner—Jeffrey A. Schmidt
Attorney, Agent, or Firm—Evenson, Wands, Edwards, Lenahan, & McKeown

[57] ABSTRACT

An arthroscopic probe having an elongated shaft with a small probing hook, which can be used for diagnostic purposes and which, for therapeutic purposes, has a longitudinally displaceable optical fiber guided at the distal end of the probing hook so that it is curved by approximately 30°.

8 Claims, 1 Drawing Sheet

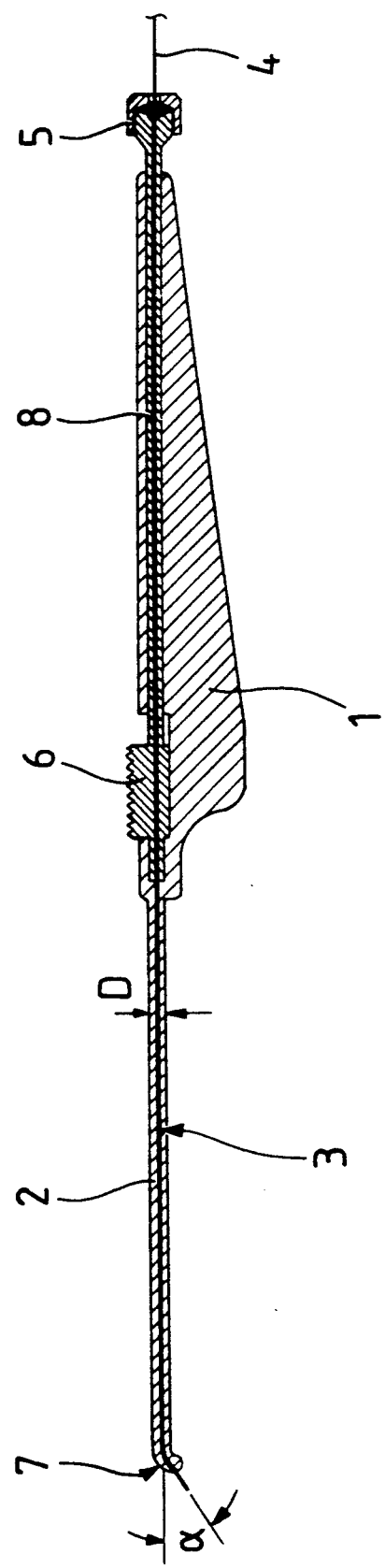

SMALL PROBING HOOK FOR ARTHROSCOPY

BACKGROUND AND SUMMARY OF THE INVENTION

The present invention relates to a small probing hook for arthroscopic use, comprising a handle connected to a shaft which is resistant to bending and which is bent at its distal end by approximately 90° with a bending radius of 2-5 mm.

In arthroscopy, the small probing hook is a standard instrument for diagnostic procedures on knee joints, as well as on shoulder, ankle and even finger and toe joints. It permits probing of the structure and the examination of the weight bearing capacity of cartilage surfaces, the strength of transverse and lateral ligaments, the anchoring of the menisci or the condition of the interior membranes of the joint. Heretofore, for the purpose of therapy, the probing hook had to be exchanged for a corresponding cutting instrument. Therefore the treatment of sites of the body that are difficult to reach, such as the posterior horn of the menisci in the knee joint gap, was not possible or was possible only to a limited extent.

German Patent Document DE 37 39 385 A1 discloses an arrangement for cutting tissue in the area of the joint by means of an excimer laser source. For the purpose of a therapy of tissue not situated along the axial direction of the shaft, this arrangement either has an optical arrangement to deflect the laser light (which is guided in the shaft by means of an optical fiber) by 90°, or alternatively the distal end of the shaft is bent by 90°, with a bending radius of 0.5 to 2.0 cm. At the same time, it is pointed out that the deformation of the glass fiber may result in a breakage in the case of such a bending angle. Taking into account the suggested bending radius, it is obvious that this device can be used for therapy only at easily accessible body parts. Because of the size of the instrument, it cannot be used, for example, in the knee joint gap. Although the embodiment which deflects the laser beam by means of optical devices is suitable for use at inaccessible points, it has the disadvantage of high construction expenditures and must be removed from the site of the operation in order to clean the light exit window. In addition, because of the nonexistent or small hook on the distal end, both suggested embodiments have the significant disadvantage that they are suitable exclusively for therapeutic procedures, and—like the known small probing hook—not for diagnostics procedures.

It is therefore an object of the present invention to provide an arthroscopic instrument for diagnostic and therapeutic purposes which permits treatment without an exchange of instruments and at the same time avoids the above-mentioned disadvantages of known constructions.

This object is achieved in a surprisingly simple manner, according to the invention by a probe having a handle and elongated shaft which is curved by approximately 90° at its distal end. The shaft has a longitudinal bore which houses a glass fiber, and means are provided for displacement of the glass fiber inside the bore so that it may be extended from the end of the bore for therapeutic purposes, and withdrawn for examination.

A principal advantage of the invention is that it is particularly easy to handle. Another advantage is that it offers user the same diagnostic capability as the known instruments, without an exchange of instruments for therapeutic uses. It also permits therapeutic procedures with cutting laser radiation, in which case during the diagnostic procedures the optical fiber is disposed in the shaft in a protected manner and is moved out for therapeutic procedures or for cleaning the tip of the optical fiber.

Other objects, advantages and novel features of the present invention will become apparent from the following detailed description of the invention when considered in conjunction with the accompanying drawings.

BRIEF DESCRIPTION OF THE DRAWING

The sole FIGURE of the drawing is a cross sectional view of a probing hook according to the invention.

DETAILED DESCRIPTION OF THE DRAWING

Referring to the FIGURE, a small probing hook according to the invention comprises a handle 1 in the shape of a gripping handle and a shaft with a diameter of approximately 2-4 mm which is connected to it. At its distal end, the shaft is bent by approximately 90°, with a bending radius of approximately 2- 5 mm so that, it may be used during diagnostic procedures to examine parts of a joint by feeling and pulling.

For therapeutic use, the probing hook is equipped with an optical fiber 4 which is displaceably disposed in a bore extending through the handle 1 and the shaft 2. The optical fiber 4 is connected—in a conventional manner not shown in detail—at the proximal end of the probing hook, by way of a glass fiber line, with a pulsed laser. The Holmium:YAG-Laser with a wavelength of approximately 2.1 $\mu$m is particularly suitable for cutting bones, cartilage, ligaments and menisci. A glass fiber consisting of quartz glass with a core diameter of approximately 200 $\mu$m is suitable for use as an optical fiber.

In the area of the distal end of the shaft, the bore 3 is curved in such a manner that the optical fiber 4 emerges from the opening 7 sloped at an angle $\alpha$ of approximately 30° with respect to the shaft axis. The thin glass fiber permits longitudinal shifting with simultaneous bending at an angle $\alpha$ without any danger of a breakage.

The longitudinal displaceability of the optical fiber 4 is an essential characteristic because, during the diagnostic application of the probing hook, the optical fiber 4 must be completely withdrawn into the bore 3 in order to avoid impairment of the patient by broken-off glass fiber pieces. For therapeutic application on the other hand, it is advantageous for the optical fiber 4 to project approximately 5 mm beyond the opening 7. Moreover, repeated displacement of the optical fiber 4 permits self-cleaning of deposits situated in the area of the tip of the optical fiber.

Displacement of the optical fiber 4 is possible because the optical fiber 4 is held in a conventional manner at the proximal end of the handle 1 in a clamp 5. In the embodiment shown, the clamp is connected with an operating device 6 in the form of a sliding key by way of a pipe section 8 in which the optical fiber 4 is disposed. By means of the sliding key, longitudinal displacement of the optical fiber 4 from the diagnostic to the therapeutic position can be achieved without putting down the instrument. The position of the sliding key, which is within an easy gripping range, permits the use of the probing hook for left-handed as well as for right-handed persons.

Since, during a diagnostic procedure, the shaft 2, which is resistant to bending, is acted upon by considerable bending forces, it is useful to enlarge the diameter D of the shaft 2 in the proximal direction.

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. An arthroscopic probe comprising;

a handle;

a stiff elongated shaft connected to said handle, said shaft having a distal end which is bent by approximately 90°, with a bending radius in the range of two to five millimeters;

said handle and said shaft having an axial bore extending therethrough, said bore being bent at the distal end of said shaft, in the same plane and direction as the bend in said shaft at said distal end, by an angle in the range of five to forty five degrees;

an optical fiber arranged in said bore and being longitudinally displaceable therein; and means on said probe for longitudinally displacing said optical fiber in said bore between a first position in which said fiber extends from an opening of said bore at the distal end of said shaft and a second position in which said fiber is withdrawn into said shaft.

2. Arthroscopic probe according to claim 1, wherein said bore is bent at the distal end of said shaft by an angle of approximately 30 degrees.

3. Arthroscopic probe according to claim 1, wherein said means for longitudinally displacing said optical fiber comprises:

a slidable member which is longitudinally displaceable within said handle, said optical fiber being fixedly connected to said slidable member; and means for longitudinally displacing said slidable member relative to said handle.

4. Arthroscopic probe according to claim 1, wherein the shaft has a larger diameter at a proximal end than at a distal end thereof.

5. Arthroscopic probe according to claim 4, wherein in said first position said optical fiber extends from said opening of said bore by a distance of from 1 to 10 mm.

6. Arthroscopic probe according to claim 4, wherein in said first position said optical fiber extends from said opening of said bore by a distance of 5 mm.

7. Arthroscopic probe according to claim 1, wherein in said first position said optical fiber extends from said opening of said bore by a distance of from 1 to 10 mm.

8. Arthroscopic probe according to claim 1, wherein in said first position said optical fiber extends from said opening of said bore by a distance of 5 mm.

* * * * *